United States Patent
Green et al.

[11] Patent Number: 5,894,032
[45] Date of Patent: Apr. 13, 1999

[54] PROCESS FOR THE MANUFACTURE OF PRINTED ORTHOPEDIC CASTING TAPE

[76] Inventors: Richard Green, 120 E. Cedar St., Livingston, N.J. 07039; Horace L. Freeman, 2217 Walker Ave., Burlington, N.C. 27215; William Robert Craft, 1033 Kingstree Ridge Dr., Winston-Salem, N.C. 27127

[21] Appl. No.: 08/859,066

[22] Filed: May 20, 1997

[51] Int. Cl.⁶ .................. B05D 3/12; B05D 1/38; B05D 3/02
[52] U.S. Cl. ............ 427/2.31; 427/176; 427/264; 427/270; 427/275; 427/288; 427/398.1; 427/412
[58] Field of Search ............... 427/2.31, 176, 427/274, 275, 276, 412, 267, 264, 398.1, 288, 270

[56] References Cited

U.S. PATENT DOCUMENTS

| | | | |
|---|---|---|---|
| 454,854 | 6/1891 | Cochrane, Jr. ............ | 427/176 |
| 755,976 | 3/1904 | White ........................ | 427/171 |
| 918,497 | 4/1909 | Bates ......................... | 427/171 |
| 1,811,497 | 6/1931 | Dennis ....................... | 427/176 |
| 1,870,825 | 8/1932 | Sprague ..................... | 101/493 |
| 2,037,254 | 4/1936 | Miller ........................ | 101/493 |
| 2,086,298 | 7/1937 | Isaac ......................... | 8/151 |
| 2,102,689 | 12/1937 | Fischer ..................... | 101/493 |
| 2,233,274 | 2/1941 | Teague ...................... | 427/176 |
| 2,413,970 | 1/1947 | Hawley, Jr. ................ | 427/176 |
| 2,998,630 | 9/1961 | Estephanian ............... | 427/176 |
| 3,058,192 | 10/1962 | Weiss ....................... | 28/163 |
| 3,632,380 | 1/1972 | Caroselli et al. ........... | 427/210 |
| 3,632,423 | 1/1972 | Kusuhara ................... | 427/412 |
| 3,647,505 | 3/1972 | Bjorn-Larsen .............. | 427/210 |
| 3,769,058 | 10/1973 | Bayer et al. ................ | 427/274 |
| 4,437,408 | 3/1984 | Arkans ...................... | 101/426 |
| 4,745,863 | 5/1988 | Takezaki ................... | 101/426 |
| 5,288,322 | 2/1994 | Hanna et al. ............... | 118/33 |
| 5,725,487 | 3/1998 | Freeman et al. ............ | 602/8 |

*Primary Examiner*—Diana Dudash
*Attorney, Agent, or Firm*—Alston & Bird LLP

[57] ABSTRACT

The present invention provides a process for the manufacture of printed orthopedic casting tapes. A knit, open mesh fibrous tape having elastic filaments extending in the length direction is stretched in a predetermined amount and a pattern is printed onto the stretched fibrous tape using a low temperature drying ink. The printed tape is thereafter passed through a drying zone maintained at a temperature of less than about 100° C. while the tape is maintained in the stretched condition. The printed tape is thereafter allowed to relax and is subsequently coated with a hardenable liquid resin.

19 Claims, 3 Drawing Sheets

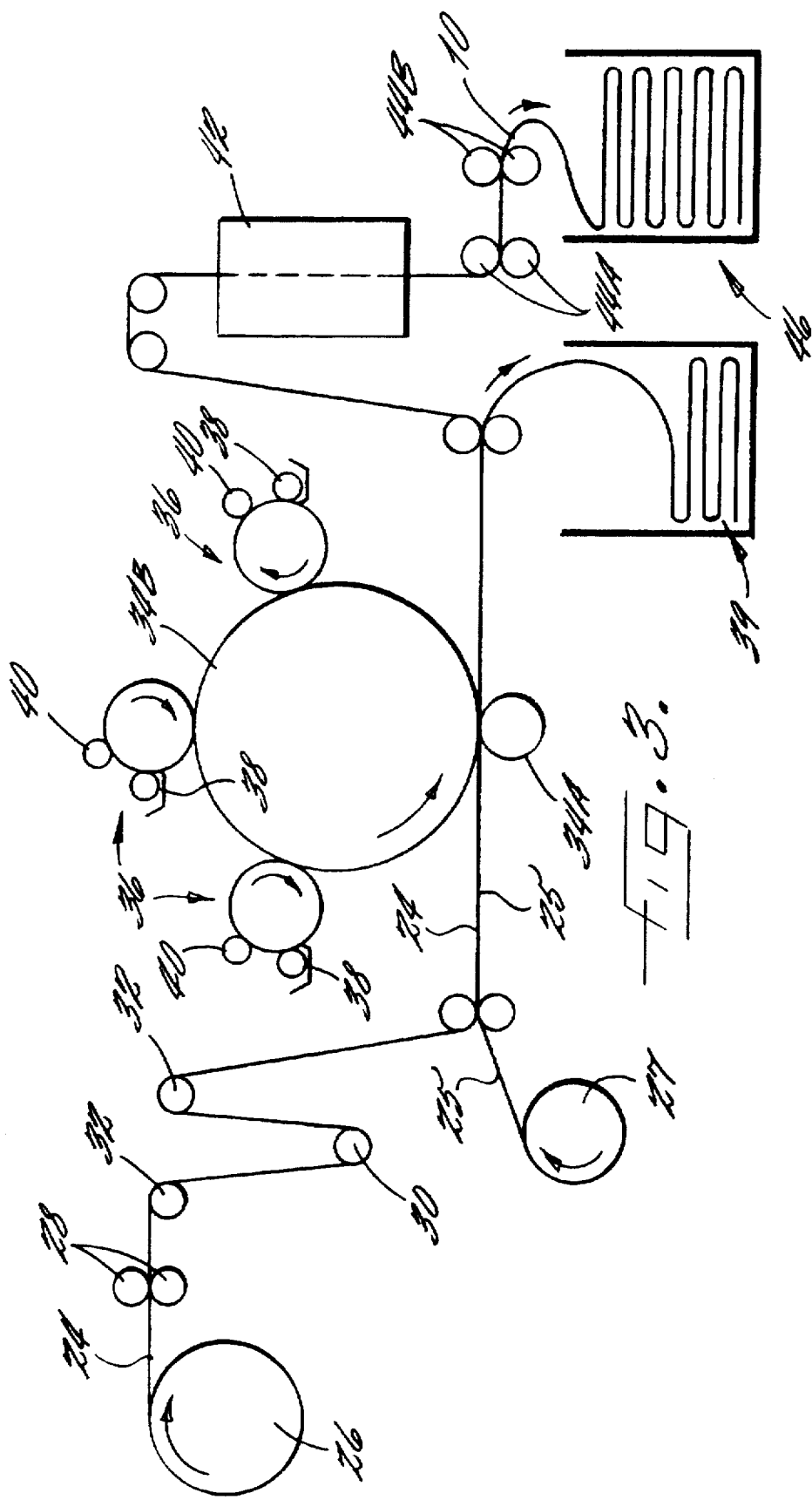

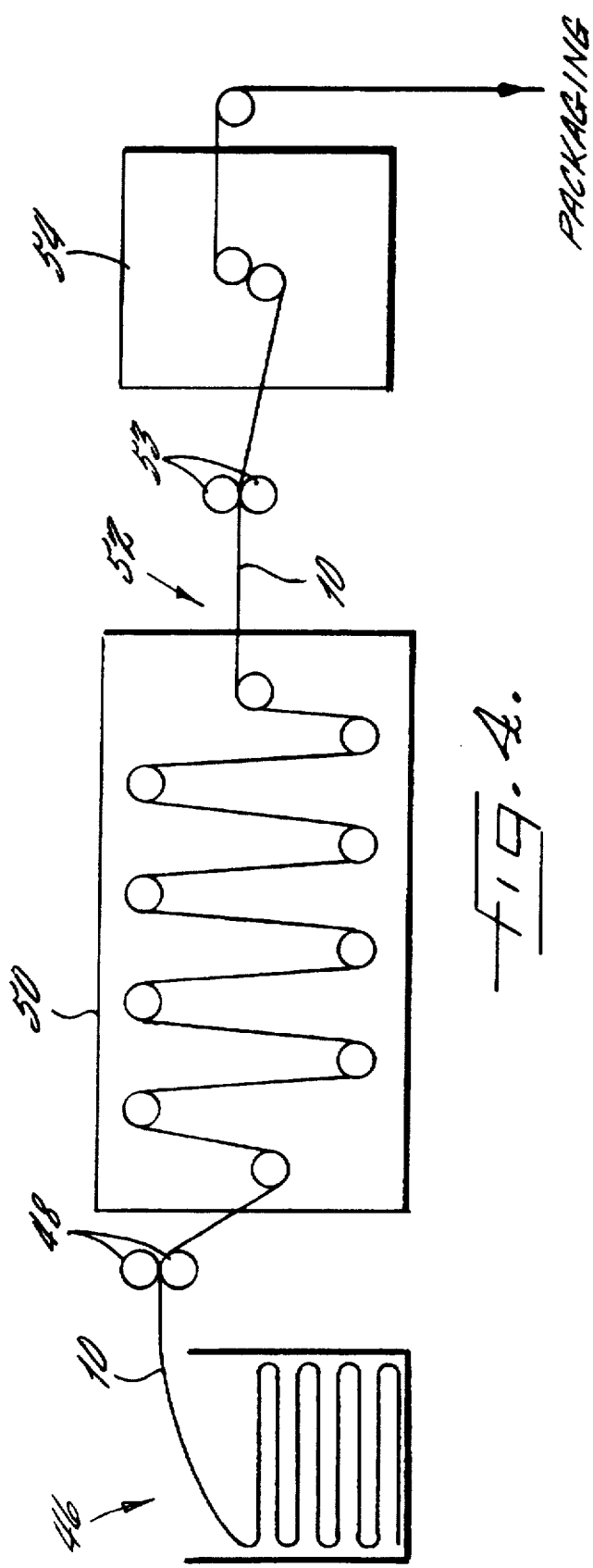

PROCESS FOR THE MANUFACTURE OF PRINTED ORTHOPEDIC CASTING TAPE

FIELD OF THE INVENTION

The invention relates to a method for manufacturing printed orthopedic casting tapes. More specifically, the invention relates to a process for manufacturing highly conformable orthopedic casting tapes bearing printed indicia of improved optical density and print characteristics.

BACKGROUND OF THE INVENTION

Synthetic orthopedic casting tapes are widely used throughout health care industries. Synthetic orthopedic casting materials are made from a liquid resin-impregnated narrow fabric or casting tape formed of glass fibers and/or synthetic fibers such as polyester, nylon, polyolefins and the like. Orthopedic casts formed from the synthetic casting materials have various advantages over conventional Plaster of Paris casts in that they are lighter, stronger and, due to the nature of the materials used, more breathable.

Water hardenable polyurethane prepolymers disclosed in Yoon, U.S. Pat. No. 4,433,680, constitute a particularly desirable hardenable liquid resin for use in synthetic casting materials. These polyurethane prepolymers, which employ a dimorpholinodiethylether catalyst, have a long shelf life during which the polyurethane polymer remains in a liquid state. When the casting tape is to be used, it is removed from a sealed package and placed in water for a few seconds. It is removed from the water and applied to the patient, usually over a tubular, knitted fabric and a padding. The bandage sets rapidly to a hardened condition in which it is capable of immobilizing a fracture.

Open mesh knit fabrics are widely used in casting tapes because of their inherent ability to stretch and because of their ability to maintain a stable mesh structure when tension is applied along the length and/or width direction of the fabric. Stretch is important because it is highly desirable that the hardened cast conform uniformly to irregular surfaces of a patient's body without causing pressure points. Stretchable narrow fabrics, i.e. tapes, can be applied to the body of a patient without requiring the formation of tucks and/or folds to compensate for irregular surfaces. High porosity, open mesh fabric structures allow the liquid resin carried by the tape to harden at a relatively fast rate and also allow the circulation of air through the hardened cast, thereby improving patient comfort.

Buese et al., U.S. Pat. No. 4,668,563, discloses high modulus casting tapes of improved conformability wherein the casting tape fabric is formed from a combination of high modulus yarns and elastic yarns. The elastic yarns are incorporated into the fabric along the length direction to give the fabric an extensibility of between 40% and 200% in the length direction. Preferably, these fabrics are Raschel Warp Knit fabrics having the elastic yarns forming or distributed within the wale yarns. The elastic yarns are incorporated into the fabric during the knitting process under a predetermined amount of tension so that the finished fabric gathers or bunches to a moderate degree when it is released from the knitting machine. The resulting fabrics are impregnated with a hardenable prepolymer to provide a casting tape of substantially improved conformability that has experienced wide-spread commercial success.

Recently, visibly patterned orthopedic casting tapes as disclosed in U.S. Pat. No. 5,088,484 to Freeman et al. have also achieved substantial commercial success. These casting tapes employ open mesh fibrous tapes bearing coloring agents which are applied to the tape in a visible pattern by various conventional processes including dyeing, sublimation dye printing and ink printing. The visible pattern formed by the coloring agent is stable in the presence of the uncured, hardenable casting resin and also in the presence of the cured, hardened resin.

Patterned casting tapes are preferably provided with colored patterns of substantial optical density and uniformity so that the colored pattern is readily visible on the finished cast. However, highly conformable casting tapes based on highly elastic casting tapes are typically stretched as they are applied to a patient, thus distorting the pattern on the casting tape and also distorting the optical density of the pattern. The distortion of the shape of a visible pattern on an open mesh, highly elastic knit fabric is non-uniform due to the phenomenon of 'necking' in which an elastic fabric contracts in its width direction as it is stretched in its length direction. Such necking behavior is particularly apparent in open mesh, highly elastic knit fabrics because of the interlocked nature of a knit fabric structure and because of the relatively low basis weight, i.e. relatively low fabric density, of open mesh knit fabrics. The impact on the printed pattern caused by stretching a highly conformable casting tape is increased by the open mesh structure of the casting tape fabric and by the nature of the fabric itself. In the relaxed state, open mesh knit fabrics based on elastic filaments are generally gathered or thickened. Accordingly, as the fabric is stretched, the optical density of the fabric is decreased both by the increase in porosity of the fabric and by the decreasing thickness of the fabric.

Distortion of visible patterns printed on elastic fabrics as a result of subsequent stretching of the fabric is known as recognized, for example, in U.S. Pat. No. 3,613,679 to Vijou. This patent proposes the application of a visible pattern to an elastic bandage of the type employed to support a sprained joint or the like by wrapping the bandage around an injured joint under tension. An undistorted pattern is applied to the elastic bandage by printing while the bandage is stretched. When the bandage is subsequently relaxed, the pattern is distorted. When the bandage is applied to a patient, a predetermined amount of tension can be applied by the bandage by stretching the bandage sufficiently to return the pattern to its undistorted state. Although in theory the variations in the distortion of the pattern should uniformly indicate a desired amount of tension on the elastic bandage, U.S. Pat. No. 4,437,408 to Arkans indicates that because elastic webs have different stretch characteristics between different lots or types of webs, changes in the geometric form are not necessarily uniform. According to this patent, uniformity of pattern distortion in elastic bandages can be achieved by printing a geometric form onto the elastic bandage while maintaining the bandage under a predetermined measured amount of tension rather than a predetermined amount of stretch.

Despite the expectation of the prior art that printing of a geometric pattern onto a stretched elastic tape under controlled tension should provide an elastic tape exhibiting the same, undistorted printed pattern when the tape is subsequently stretched the same amount as it was stretched during printing, it has been found that open mesh, knit orthopedic casting tapes based on elastic filaments do not uniformly follow the expected behavior. Thus when printed under tension using conventional printing processes and thereafter coated with liquid resin using conventional coating equipment, these tapes in many cases do not exhibit an undistorted pattern when they are subsequently stretched in about the same amount as during printing. There are substantial differences between open mesh casting tapes and elastic bandages including substantial differences in the power of the tapes. The low power of casting tapes renders these tapes more susceptible to stretching upon variations in tension. In addition, thickness changes and necking are more pronounced in casting tapes upon stretching.

SUMMARY OF THE INVENTION

The present invention provides highly conformable orthopedic casting tapes comprising elastic filaments and bearing printed indicia of improved optical density and print characteristic. The orthopedic casting tapes of the invention can be manufactured using readily available offset printing equipment which provides considerable flexibility in manufacturing short runs of different patterns. The casting tapes are highly elastic casting tapes of relatively low retractive power yet provide highly uniform distortion of a printed pattern as the casting tape is stretched even following coating with a hardenable liquid resin but prior to the hardening thereof.

In accordance with the invention, a knit, open mesh fibrous tape having elastic filaments extending in the length direction is stretched a predetermined amount, and then a nondistorted pattern is printed onto the fibrous tape using a low temperature drying ink. The printed tape is thereafter passed through a drying zone maintained at a temperature of less than about 100° C., preferably less than 80° C. while the tape is maintained in the stretched condition. The printed tape is thereafter allowed to relax and is subsequently coated with a hardenable liquid resin. The use of low temperature drying inks and low temperature drying of the inks in accordance with the invention is believed to stabilize the tape against variations in elasticity during or after printing. The stretch and relaxation behavior of the printed patterns on the casting tapes is substantially improved over tapes printed using conventional inks which are dried at temperatures above 150° C. while the tape is stretched. It is also preferred that the tape be supported on an ink-receptive backing during the printing step. The backing absorbs ink that passes through the enlarged mesh opening and might otherwise be smeared onto the bottom surface of the tape.

Preferably, the knit, open mesh tape is formed primarily or substantially entirely of unbulked, continuous polymeric filaments and elastic filaments. Advantageously, the knit fibrous tape includes at least about 15 courses per linear inch of tape, measured in a relaxed state, and, more preferably at least about 17 up to about 22 courses per inch of tape. The wales are advantageously present in an amount sufficient to provide at least about 275 openings per square inch.

The casting tape has an extensibility prior to coating of at least about 25%, preferably 30% or higher, and is advantageously printed while maintained under an extension of at least about 20%. Preferably, the degree of stretch applied to the tape during printing is less than the recommended amount of extension applied to the liquid resin coated casting tape during use thereof, i.e., during application of the casting tape to an injured limb or other area of a patient. In preferred embodiments of the invention, the recommended stretch of the coated tape is about 35-45% and the tape is stretched about 25-30% during printing.

In accordance with another aspect of the invention, the knit, open mesh fibrous tape is advantageously subjected to a drying treatment just prior to being coated with liquid resin. According to this embodiment of the invention, the tape is passed through a heated drying zone maintained at a temperature of up to about 100° C. while the tape is maintained under substantially no tension. The tape is subsequently recovered from the drying zone, cooled and thereafter stretched and coated with a hardenable liquid resin while maintained in said stretched condition. This aspect of the invention is particularly desirable for use with tapes formed from synthetic fibers and elastic filaments.

While not wishing to be bound by any particular theory, it is believed that the use of low temperature drying inks and minimizing the exposure of the highly elastic tape to conditions of high temperature while it is in the stretched state improves the uniformity of stretch behavior of the tape during the printing operation and also decreases the likelihood of changing the stretch properties of the tape during the printing process. High temperatures are believed particularly undesirable because the knit casting tape has relatively low power, (the force necessary to stretch a fabric by a given percentage in order to prevent constriction of a patient's limb after the tape is applied to the patient and before the resin cures). The need for low power in an orthopedic casting tape fabric is discussed in greater detail in U.S. Pat. No. 4,668,563 to Buese et al., which is hereby incorporated by reference. Although many elastic filaments are known to change their stretch properties either temporarily or permanently upon the application of heat, the desirably low power of the orthopedic casting tape together with the open structure of the fabric are believed to render the tape more susceptible to stretch variations due to the application of heat.

In addition, it is believed that applying a printed pattern to the tape while maintaining the tape at a stretch level below the level of stretch expected to be applied to the tape as it is applied to a patient minimizes any permanent decrease in the stretch characteristics of the tape that might be caused by the printing process. In this regard, the ink pickup is less than would be achieved in a printing process using a more stretched tape. Moreover, the degree of stress applied to the elastic yarns while the tape is heated for drying of the inks, is also decreased. Even though the undistorted printing pattern is applied to the tape while it is stretched to a lesser degree than it is stretched as it is applied to a patient, it has been found that the geometric pattern exhibited by the tape in the final cast in its hardened state corresponds with substantial correlation to the initial printed pattern applied to the tape.

BRIEF DESCRIPTION OF THE DRAWINGS

In the drawings which form a portion of the original disclosure of the invention:

FIG. 3 is a diagrammatic view of one preferred apparatus for the manufacture of a printed orthopedic casting tape in accordance with a preferred embodiment of the invention; and FIG. 4 is a schematic view illustrating a preferred apparatus for drying the knit, open mesh printed fabric illustrated in FIGS. 1 and 2 under conditions of substantially no tension, followed by cooling and stretching the fabric, and thereafter coating the fabric with a liquid resin while maintaining the fabric in a stretched condition.

DETAILED DESCRIPTION OF THE PREFERRED EMBODIMENTS

Figure 1:
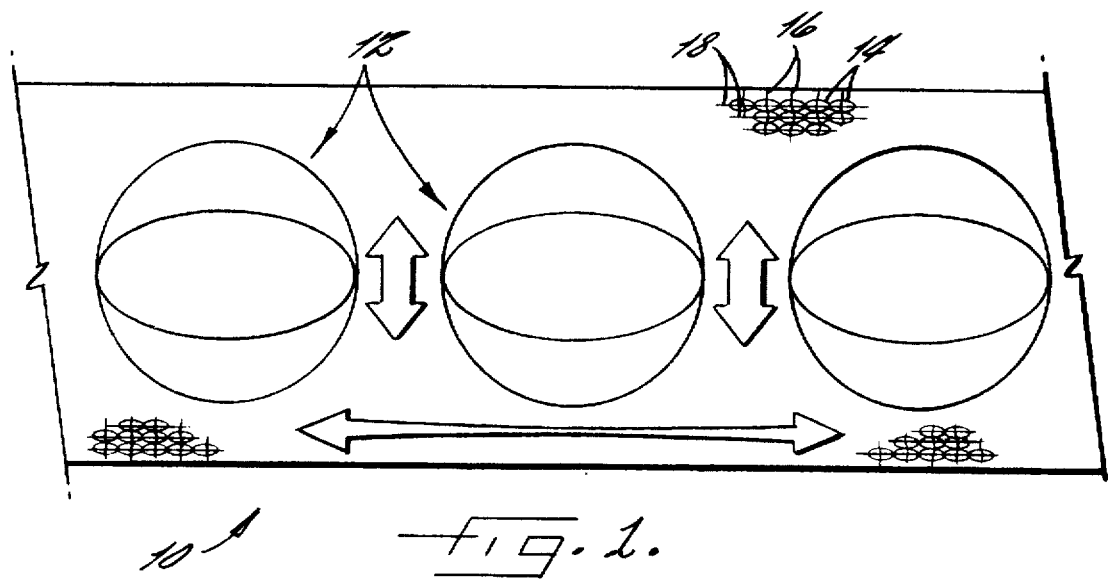
FIG. 1 is a top plan view illustrative of a visibly patterned casting tape of the invention and illustrates the tape in a stretched condition bearing a printed pattern in the undistorted form in which it is applied to the tape during printing.

In the following detailed description, preferred embodiments of the invention are discussed in detail to enable practice of the invention. It will be apparent that although specific terms are used to describe the preferred embodiments, these are used in the descriptive sense and not for the purpose of limiting the invention thereto. It will also be apparent that the invention is susceptible to numerous changes and may be embodied in many different forms other than the preferred embodiments specifically described below as will become apparent from a consideration of the invention as shown in the attached drawings and described below. In the drawings, like numbers refer to like elements throughout.

FIG. 1 diagrammatically illustrates a visibly patterned, knit, open mesh casting tape 10 in a stretched condition bearing a visible printed pattern 12 in an undistorted form as it is applied to the tape during printing. The knit, open mesh casting tape 10 is a highly elastic narrow fabric defined by a plurality of wales and courses, generally illustrated as yarns 14 and 16, respectively. The wales 14 extend longitudinally along the casting tape and the courses 16 extend generally transverse to the wales 14, i.e., the courses 16 extend in the width direction of the casting tape 10. The courses 16 and wales 14 are advantageously made from any of various natural and/or synthetic yarns including yarns made from polyesters such as polyethylene terephthalate; polyolefins such as polypropylene; polyamides such as nylon 6 and nylon 6,6; glass; carbon; cotton; rayon; and the like. A portion, or all of the wales 14 include an elastic extensible yarn illustrated generally as yarn 18. The term 'yarn' as used herein includes any of various well known yarn structures including yarns formed from monofilament and multifilament continuous filamentary materials, spun yarns formed from staple fibers and the like.

Figure 2:
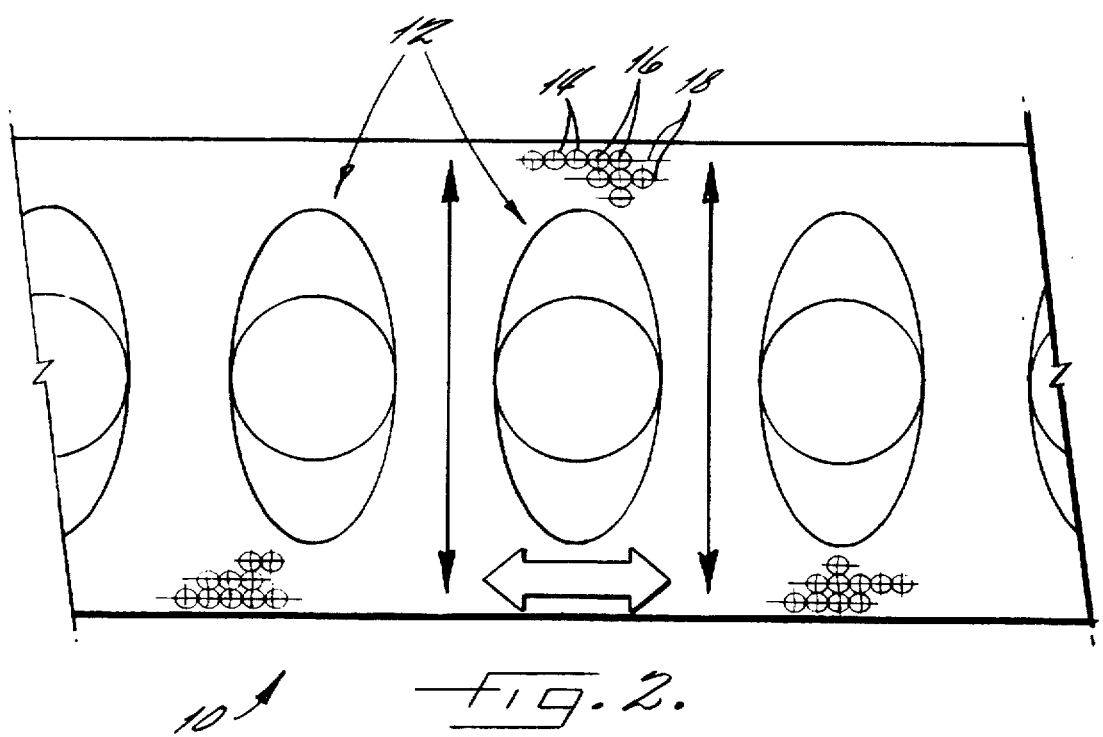
FIG. 2 is a top plan view illustrative of a visibly patterned casting tape of the invention and illustrates in exaggerated form the printed tape of FIG. 1 in a relaxed condition following drying of the printed pattern. As illustrated, the tape has contracted in the length direction and expanded in the width or cross-machine direction and the printed pattern has been similarly distorted.

FIG. 2 diagrammatically illustrates the visibly patterned, knit, open mesh casting tape 10 shown in FIG. 1 in a relaxed condition following drying of the printed pattern 12. As seen by a comparison of FIGS. 1 and 2, the relaxed tape of FIG. 2 has contracted in the length direction. However, the relaxed elastic tape of FIG. 2 is seen to have grown larger in the width or cross-machine direction due to the phenomenon of necking in which an elastic fabric contracts in its width direction as it is stretched in its length direction. Necking behavior is particularly apparent in open mesh, highly elastic knit fabrics because of the interlocked nature of a knit fabric structure and because of the relatively low basis weight, i.e. relatively low fabric density, of open mesh knit fabrics.

As also seen by a comparison of FIG. 1 and FIG. 2 the printed pattern 12 is distorted as the highly elastic knit tape 10 is stretched and relaxed. Thus as tension is applied to the relaxed tape fabric of FIG. 2, the pattern 12 changes into the longer and narrower shape seen in FIG. 1. In addition to the change in the shape of the pattern, the optical density of the pattern 12 is also changed as the knit tape 10 is stretched or relaxed. Because of the relatively low fabric density of open mesh knit tape 10, the courses 16 forming the cross-direction yarns of the tape 10 move away from each other as the fabric is stretched, while the wales, forming the lengthwise yarns of the tape 10 move closer together. Thus as the fabric is stretched, the optical density of the visible pattern 12 decreases along the length of the pattern 12 while increasing across the width of the pattern 12.

Because highly elastic casting tapes are designed to stretch substantially as they are applied to a patient, prior to hardening of the liquid resin, a visible printed pattern on the tape is distorted in both its shape and its optical density characteristics for the reasons discussed above. These undesirable distortions are overcome in accord with the present invention by applying a printed pattern to the open mesh knit tape 10 while the tape 10 is maintained in a stretched condition. This provides substantial control over both the shape and the optical density characteristics of the pattern 12 on the open mesh casting tape 10 when the tape is applied to a patient in a stretched condition, and subsequently hardened on the patient in the stretched condition.

The knit, open mesh casting tape 10 can be formed from a variety of yarns and in a variety of knit structures. Although the wales 14 and courses 16 can be made from glass or other inorganic, or synthetic polymer high modulus yarns, e.g., high modulus polyethylene terephthalate yarns formed from high intrinsic viscosity (IV) polymer of the type normally used in industrial end uses such as in tires and v-belts, or from various natural fibers such as cotton or wool, the courses 16 and wales 14 are advantageously made from synthetic multifilament continuous yarns having a low affinity for moisture including yarns made from polyesters, preferably polyethylene terephthalate, or polyolefins, preferably polypropylene. Moisture absorbing yarns can complicate the polymer coating process when the preferred water activatable polymers are employed and can interfere with the shelf life of the preferred packaged product and are not preferred for this reason. Polyethylene terephthalate continuous yarns are presently preferred for forming wales 14 and courses 16.

Advantageously, the synthetic continuous multifilament yarns are unbulked or 'flat' yarns, i.e., yarns that are substantially free of texturing or other processing for substantially increasing bulk, and are of textile grade intrinsic viscosity and tenacity, i.e., the yarns preferably have a tenacity of less than about 8 grams per denier, more preferably less than about 7 grams per denier, which increases the conformability and smoothness of the final casting tape. As disclosed in detail in copending U.S. patent application Ser. No. 08/481,912, now U.S. Pat. No. 5,725,487, filed Aug. 24, 1995 by Freeman et al. which is hereby incorporated by reference, it has recently been found that such textile grade, continuous multifilament flat yarns having total deniers as low as 150 denier can be used to form both courses and wales in combination with elastic filaments incorporated into the wales to provide final hardened casts having strength properties comparable to or exceeding the strength properties of conventional hardened casts of comparable fabric weight glass fabrics.

The orthopedic casting tapes 10 are highly elastic tapes having an extensibility along the length direction of the fabric of at least about 25%, preferably at least about 30%, more preferably at least about 40%. Extensibility is measured by applying a weight of 1.5 lbs. per inch width of the casting tape to a sample of the uncoated casting tape, i.e., knit fabric, which has a length of 10 inches for a time sufficient that elongation is substantially unchanging. Extensibility is calculated by expressing the increase in length as a percentage of the original tape length, wherein the term extensibility, as used herein, applies to elongations which are at least about 60%, preferably at least about 70%, recoverable when the weight is removed within a short time following stabilization of elongation. It is also preferred that the extensibility of the tape be maintained to an amount less than about 100%. In highly preferred embodiments of the invention, the tape has an extensibility prior to coating, in the range of about 40% to about 85%, and even more preferably, the extensibility is in the range of about 60% to about 70%. As discussed in U.S. Pat. No. 4,668,563 to Buese et. al., the power (retractive) of an orthopedic casting bandage should be low to prevent constriction of the patient's limb after the tape is applied to the patient and should be maintained within the range of between about 40 and 175 grams per inch tape width based on a fabric stretch of 30%.

In order to provide the highly elastic casting tape fabric, all or a portion of the wales 14 include an elastic extensible yarn 18 therein. Preferably the elastic yarn is formed of an elastomeric material, i.e., a fiber forming material which provides an inherent stretch and recovery. The elastic extensible yarn can be formed of an acid treated natural rubber or a synthetic thermoplastic elastomer such as polyisoprene, polybutadiene, styrene-diene copolymers including di- and tri-block copolymers of styrene with butadiene, isoprene, or saturated or unsaturated ethylene-propylene copolymer blocks such as the KRATON™ elastomers, copolymers of acrylonitrile and a diene, polychloroprene, copolymers of polychloroprene and other monomers, ethylene-propylene thermoplastic elastomers including ethylene-propylene copolymers and ethylene-propylene-diene terpolymer elastomers and block copolymers of ethylene and butene, hexene, octene, decene, or 4-methylpentene, commercially available as Exact™ resins, polyester-polyether elastomers commercially available as Hytrel™ resins, polyurethanes, elastomers based on polyurethanes and polyethers including materials commercially available as Pellathane™, silicone elastomers including-high molecular weight linear divinyl polydimethylsiloxanes and silicone hydride cross-linked polymers thereof, polyether-polyamide elastomers available as Pebax™, and the like.

Yarns formed of a dynamically vulcanized blend of olefin rubber and thermoplastic olefin resin, such as those disclosed in U.S. Pat. No. 4,130,535, and preferably a dynamically vulcanized blend of polypropylene and EDPM rubber, commercially available as Santoprene®, are currently preferred because it has been found that these yarns are substantially inert to water-activatable polyurethane resins so as to provide the casting tape with a shelf life of between two and four years, while maintaining a recoverable elongation of about 70%.

The elastic yarns 18 are preferably included in at least about one fourth, preferably at least about one third of the wales and are preferably distributed across the width of the fabric substantially uniformly, e.g., every fourth or every third wale, every other wale, or every wale, etc. Most preferably, the elastic yarns 18 are included in all of the wales and are thus distributed across the width of the fabric uniformly. Fabric structures incorporating elastic yarns into the wales of the fabric are disclosed in the aforementioned Buese et al. patent and in the previously mentioned U.S. patent application Ser. No. 08/481,912.

The orthopedic casting tape 10 can be knit on various and numerous knitting apparatus and is advantageously knit on a Raschel Warp Knitting apparatus. Preferably, the knitting machine should exceed about 10–12 needles per inch depending on yarn denier and the number of courses per inch, and more preferably, should include from about 14 to about 28 needles per inch, for example, about 18 needles per inch. In practice, the knit fabric will typically contract substantially both along its length (machine direction) and across its width (cross-machine direction) due to the inclusion of elastic yarns some or all of the wales. In the finished state, the casting tapes are typically provided in widths ranging from about two inches (5 centimeters) to about 5 inches (about 13 centimeters); however during the knitting process, the knit tape will normally have a greater width and increased length.

The knitting process is preferably conducted to provide uniform and closely spaced continuous filament courses in an amount of at least about 15 courses per linear inch of tape, measured in a relaxed state. Preferably, there are at least about 16 courses per linear inch of tape, more preferably, there are between about 17 and about 22 courses per inch of tape. The wales are provided in the in the fibrous tape in an amount sufficient, based on the number of courses, to provide at least about 275 openings per square inch in preferred embodiments. The number of courses and wales can be varied depending on factors such as yarn denier and strength, and also depending on the fabric weight, smoothness, strength, and number of mesh openings desired in the final orthopedic casting tape.

Referring now to FIG. 3, a preferred printing process in accordance with the invention employing a multiple color rotary offset printing machine is illustrated. Rotary offset printing machinery for printing of tape fabrics is well known and is commercially available from various sources including, for example, CDS Italia S.R.I.

Highly elastic knit tape 24 is continuously supplied from a supply roll or in loose form from a supply 26 to the nip of a pair of dry rolls 28. An ink receptive backing 25 is also continuously supplied from a supply roll 27. Preferably, the ink receptive backing is moisture and ink absorptive. For example, tissue paper has been found to be an effective backing. The ink receptive backing 25 has a width at least as wide as the width of knit tape 24 and is positioned below the knit tape, in contact therewith. The elastic tape is stretched to a predetermined amount by speed differences between nip rollers 28 and the nip between the print cylinder 34B and roll 34A. The speed of nip rollers 28 may be adjusted independently from the speed of the printing cylinder by changing a reostat which controls the speed of the DC motor driving nip rollers 28. The ink receptive backing 25 is driven along with the elastic knit tape 24. As shown, the ink receptive backing 25 is supplied adjacent the knit tape supply roll. It is within the scope of the invention, however, to position the ink receptive supply in other locations upstream from the print cylinder 34B and roll 34A.

Constant tension is controlled by a dancer roll 30 which trims the speed of rollers 28. The dancer roll 30 acts in cooperation with a pair of support rolls 32 to apply tension to the unprinted tape. The use of dancer rolls for applying tension to various textile materials is well known in the art and generally involves the use of a predetermined weight on the idle roller 30 which is vertically movable and a means of transmitting vertical movement to an encoder or similar mechanism which transmits an electronic signal to the DC motor of drive rollers 28.

Preferably, the idle roll 30 applies a force to the unprinted tape 24 of between about 30 and about 80 grams/in. width of tape, preferably between about 40 and about 70 grams/in. width of tape, most preferably between about 50 and about 60 grams/in. width of tape. Because the power of the tape is relatively low, i.e. preferably between 40 and 175 grams/in. width to stretch the fabric 30%, more preferably between about 40 and 175 grams/in. width to stretch the fabric 30%, the degree of stretch applied to the fabric is preferably between about 20 and about 40%, more preferably between about 25 and about 30%.

The stretched fabric is thereafter contacted by the printing drum 34B and nip roller 34A of a conventional rotary offset printing machine. The rotary offset printing machine includes at least one, and preferably a plurality of inking stations 36 that each include a moisture applying roll 38 and one or more ink rolls 40. Each of the inking stations apply one color of a multiple color pattern to the surface of the print roll 34, which in turn applies the multiple color printed pattern to the surface of the stretched unprinted tape 24. In accordance with a preferred aspect of the present invention, the ink receptive backing 25 provides an ink absorbing material to receive ink that passes through the enlarged mesh opening of the stretched fabric and therefore does not adhere to the open mesh tape 24. Accordingly, the nip roller 34A remains substantially free of residual ink or moisture which passes through the open mesh tape 24. Also, the underside of the tape 24 likewise does not come into contact with unnecessary moisture or residual ink that could distort the print pattern applied to the tape. The ink receptive backing 25 may thereafter be removed from the process. For example, a collection container 39 may be provided to collect the backing 25. Alternatively, the backing 25 may be contiguous with the tape throughout the drying process and may even remain with the tape in the end product.

The ink applied by the ink rolls 40 at each of the printing stations 36 is a low temperature rapid drying ink, typically based on a mixture of a hardenable resin, a pigment, and a heat activatable curing or crosslinking agent. Preferably, the inks are based on air curable resins such as vegetable oils, for example linseed oils and modified soy oils, together with a heat-activatable crosslinking agent such as cobalt and manganese tallate. As will be apparent, the ink, following curing, must be stable in the presence of the hardenable liquid casting resin which is later applied to the printed tape, and additionally must not cause premature hardening of the hardenable liquid resin. Various low temperature drying inks are available as will be apparent to those of ordinary skill in the art. Preferred inks can be obtained from VanSon Holland Ink Corporation of America under the trade name Dura-Tuf.

The inks applied to the tape 24 by the print roll 34 are initially wet and can be smeared by relaxation of the fabric prior to drying of the ink. The printed stretched fabric is accordingly passed through a low temperature heating zone 42 wherein the ink is dried by low temperature heating. In accordance with the present invention, it has been found that conventional heating zones which normally heat an ink to a temperature well above 150° C. in order to dry the ink can interfere with the stretch characteristics of the tape 24 either during the printing process and/or can "kill" a portion of the elasticity of the tape, which in turn changes the pattern distortion characteristics of the tape. In accordance with the present invention, the heating zone is advantageously maintained at a temperature of less than about 100° C., preferably less than about 80° C., more preferably about 65–70° C. which is a temperature sufficient to dry the low temperature drying inks discussed above. The knit elastic tape bearing the dried printed pattern is removed from the drying zone 42 via a pair of drive rollers 44A and then the tape is moved vertically to a pair of drive rollers 44B and then the tape is allowed to relax and may be stored in roll form under substantially no tension or is preferably festooned into a container under substantially no tension as generally illustrated at 46 in FIG. 3.

The printed tape 10 is preferably stored for a period of at least about 72 hours prior to further processing. This allows the dry ink to achieve a full cure which both stabilizes the printed pattern on the elastic tape and prevents the ink from chemically interacting with the curable liquid resin which is later applied to the tape.

Following curing of the ink, the printed tape is coated with a hardenable liquid resin, preferably a polyurethane prepolymer. The prepolymer is applied in a dry atmosphere to the printed tape by any of various processes, preferably a reverse roll coating technique known for forming cast bandages. The weight of prepolymer on the fabric can range from about 60 to about 400 grams per square meter, preferably from about 80 to about 300 grams per square meter to thereby provide a prepolymer weight of between about 30% and 70% by weight, based on the weight of the coated tape. The skilled artisan will recognize that the amount of prepolymer will depend in part on the nature and composition of the fibrous tape and on the specific tape construction. Immediately after the prepolymer is applied to the fabrics the coated tape is packaged in an inert atmosphere to prevent any contact with atmospheric moisture.

As indicated previously, numerous polyurethane prepolymers are known and can be successfully employed in the invention. The preferred polyurethane prepolymers are disclosed in U.S. Pat. No. 4,433,680 to Yoon which is hereby incorporated by reference.

Preferably, a drying treatment is applied to the printed tape prior to coating with the hardenable liquid resin in accordance with another preferred aspect of the invention as illustrated in FIG. 4. In general, offset printing inks have been found susceptible to moisture pickup. In addition, the offset printing process typically applies water to the elastic tape during the printing process and accordingly, it is desirable to dry the printed tape just prior to coating with the hardenable liquid resin. In accordance with this aspect of the invention, it has been found that to preserve the preferred distortion characteristics of the printed elastic tape, the drying treatment is conducted while the tape is maintained under substantially no tension, that is, with substantially no stretch being applied to the printed elastic tape.

As illustrated in FIG. 4, the printed tape 10 is removed from the containers 46 under substantially no tension and is fed via a pair of feed rolls 48 through a continuous drying oven 50. In the oven 50, the tape is advantageously heated to a temperature of up to about 100° C., preferably to a temperature less than about 80° C. The tape is removed from the heating oven 50 and is cooled, in zone 52 while the tape is still maintained under substantially no tension. The cooling zone 52 may be a zone wherein the tape is simply exposed to ambient temperature conditions, preferably under low humidity, sufficiently long for the tape to cool. Thereafter, the tape is tensioned and coated with a hardenable liquid resin via reverse roll coating apparatus 54.

Highly elastic casting tapes prepared in accordance with preferred embodiments of the invention have been found to exhibit high optical density patterns in the stretched state as the tape is applied to a patient and thereafter allowed to harden. In preferred embodiments of the invention, the recommended stretch for the orthopedic casting tape following coating with liquid resin is about 40%. The recommended stretch of a particular orthopedic casting tape can be determined from the manufacturer's literature accompanying the tape by comparing the stated tape length to the relaxed tape length. The stated tape length is typically the length of the tape when stretched to the recommended amount. Thus, a orthopedic casting tape with a stated length of 1.4 meters that has a length when relaxed of one meter has a recommended stretch of 40%, as will be apparent.

The invention has been described in considerable detail with reference to its preferred embodiments. However, numerous modifications and variations may be made without departing from the spirit and scope of the invention as described in the foregoing specification and defined in the appended claims.

That which is claimed:

1. The process for manufacturing a printed orthopedic casting tape comprising the steps:
   (a) stretching a knit, open mesh elastic fibrous tape having elastic filaments extending in the length direction in an amount greater than about 20%;
   (b) printing a visible pattern onto said fibrous tape, said printed pattern being formed by a wet ink of at least one color, said ink being capable of drying at a temperature of less than about 100° C.;
   (c) passing the printed fibrous tape through a heating zone maintained at a temperature of less than about 100° C. while maintaining the printed fibrous tape in the stretched condition and recovering from said heating zone the printed fibrous tape wherein said ink is in substantially dry form; and
   (d) thereafter coating said printed fibrous tape with a liquid resin capable of curing to form a hardened plastic.

2. The process of claim 1 wherein said heating zone is maintained at a temperature of less than about 80° C.

3. The process of claim 2 wherein said knit elastic fibrous tape stretched in said stretching step has an extensibility of at least about 30%.

4. The process of claim 3 wherein said knit elastic fibrous tape has an extensibility of less than about 100%.

5. The process of claim 1 wherein said elastic filaments comprise a thermoplastic elastomer.

6. The process of claim 2 wherein said knit elastic fibrous tape is formed substantially entirely of unbulked, continuous polymeric filaments and elastic filaments.

7. The process of claim 6 wherein said knit elastic fibrous tape stretched in said stretching step has an extensibility of at least about 40%.

8. The process of claim 2 wherein said knit elastic fibrous tape is stretched in an amount of at least about 25% during said stretching step.

9. The process of claim 2 wherein said knit elastic fibrous tape comprises at least about 275 openings per square inch in a relaxed state.

10. The process of claim 9 wherein said knit elastic fibrous tape comprises at least about 16 courses per linear inch in the relaxed state.

11. The process of claim 2 wherein said tape is stretched in said stretching step by applying to said tape a tension of less than about 80 grams per inch width of tape.

12. The process of claim 11 wherein said tape has a power of less than about 175 grams per inch tape width based on a fabric stretch of 30%.

13. The process of claim 12 wherein said tape is composed substantially entirely of synthetic polymeric and elastic filaments.

14. The process of claim 13 wherein said synthetic polymeric filaments comprise polyethylene terepthalate filaments.

15. The process of claim 2 wherein said ink comprises at least one pigment, a hardenable resin comprising an air curable vegetable oil resin, and at least one heat-activatable crosslinking agent.

16. The process according to claim 1 wherein said knit fibrous tape is supported on an ink receptive backing, at least during said printing step.

17. The process for manufacturing a printed orthopedic casting tape comprising the steps:
   (e) stretching a knit, open mesh elastic fibrous tape having elastic filaments extending in the length direction in an amount greater than about 20%;
   (f) printing a visible pattern onto said fibrous tape, said printed pattern being formed by a wet ink of at least one color, said ink being capable of drying at a temperature of less than about 100° C.;
   (g) passing the printed fibrous tape through a heating zone maintained at a temperature of less than about 100° C. while maintaining the printed fibrous tape in the stretched condition and recovering from said heating zone the printed fibrous tape wherein said ink is in substantially dry form;
   (h) relaxing said printed tape;
   (i) allowing said dried ink to cure for a period of at least about three days; and
   (j) thereafter coating said printed fibrous tape with a liquid resin capable of curing to form a hardened plastic.

18. The process of claim 17 further comprising the step following said curing step of passing said printed tape through a heated drying zone maintained at a temperature of less than about 100° C. while maintaining said tape in an essentially tension free state.

19. The process of claim 18 further comprising the step of recovering a dry printed tape from said heating zone maintained at said temperature of less than about 100° C., cooling said tape while maintaining said tape in a tension-free state, applying tension to said cooled tape and maintaining said tape under said applied tension during said coating step.

* * * * *